(12) United States Patent
Abeywardena et al.

(10) Patent No.: US 9,750,782 B2
(45) Date of Patent: Sep. 5, 2017

(54) COMPOSITION AND METHOD FOR IMPROVING VASCULAR HEALTH

(71) Applicant: MALAYSIAN PALM OIL BOARD, Kajang, Selangor (MY)

(72) Inventors: Mahinda Abeywardena, Coromandel Valley (AU); Ravigadevi Sambanthamurthi, Selangor Darul Ehsan (MY); Yew Ai Tan, Kuala Lumpur (MY); Kalyana Sundram P. Manickam, Selangor Darul Ehsan (MY); Mohd Basri Wahid, Selangor Darul Ehsan (MY)

(73) Assignee: MALAYSIAN PALM OIL BOARD, Kajang, Selangor (MY)

( * ) Notice: Subject to any disclaimer, the term of this patent is extended or adjusted under 35 U.S.C. 154(b) by 0 days.

(21) Appl. No.: 14/322,564

(22) Filed: Jul. 2, 2014

(65) Prior Publication Data

US 2014/0314875 A1    Oct. 23, 2014

Related U.S. Application Data

(62) Division of application No. 13/376,628, filed as application No. PCT/MY2010/000096 on Jun. 8, 2010, now Pat. No. 8,771,764.

(30) Foreign Application Priority Data

Jun. 9, 2009 (MY) ................................ PI20091963

(51) Int. Cl.
| | | |
|---|---|---|
| *A61K 36/889* | (2006.01) | |
| *A61K 45/06* | (2006.01) | |
| *A23L 33/105* | (2016.01) | |

(52) U.S. Cl.
CPC .......... *A61K 36/889* (2013.01); *A23L 33/105* (2016.08); *A61K 45/06* (2013.01); *A23V 2002/00* (2013.01)

(58) Field of Classification Search
CPC ..................................................... A61K 36/889
USPC ......................................................... 424/727
See application file for complete search history.

(56) References Cited

U.S. PATENT DOCUMENTS

| | | | |
|---|---|---|---|
| 7,387,802 B2 | 6/2008 | Sambanthamurthi et al. | |
| 8,071,143 B2 * | 12/2011 | Hayes et al. | 424/777 |
| 2003/0031740 A1 * | 2/2003 | Sambanthamurthi et al. | 424/777 |
| 2010/0144892 A1 * | 6/2010 | Wu | A21D 13/04 514/738 |
| 2010/0183786 A1 | 7/2010 | Tan et al. | |

FOREIGN PATENT DOCUMENTS

| | | |
|---|---|---|
| WO | WO 2008/127086 | 10/2008 |
| WO | WO 2009/146102 | 12/2009 |

OTHER PUBLICATIONS

"Freeze—Dry Foods" www.freeze-dry.com/technology.html.*
Glycerol—Wikipedia.*
International Search Report dated Sep. 2, 2010 for International Application No. PCT/MY2010/000096, 4 pages.

* cited by examiner

*Primary Examiner* — Chris R Tate
*Assistant Examiner* — Deborah Davis
(74) *Attorney, Agent, or Firm* — Merchant & Gould P.C.

(57) ABSTRACT

The present invention relates to a composition for the use in improving vascular health, including treating and preventing vascular diseases and diseases related thereto, using a botanical extract of oil palm vegetation liquor from the palm oil milling process.

8 Claims, 7 Drawing Sheets

Figure 1. Vascular relaxation actions of OPP (aortic rings)

Figures 1A, 1B:
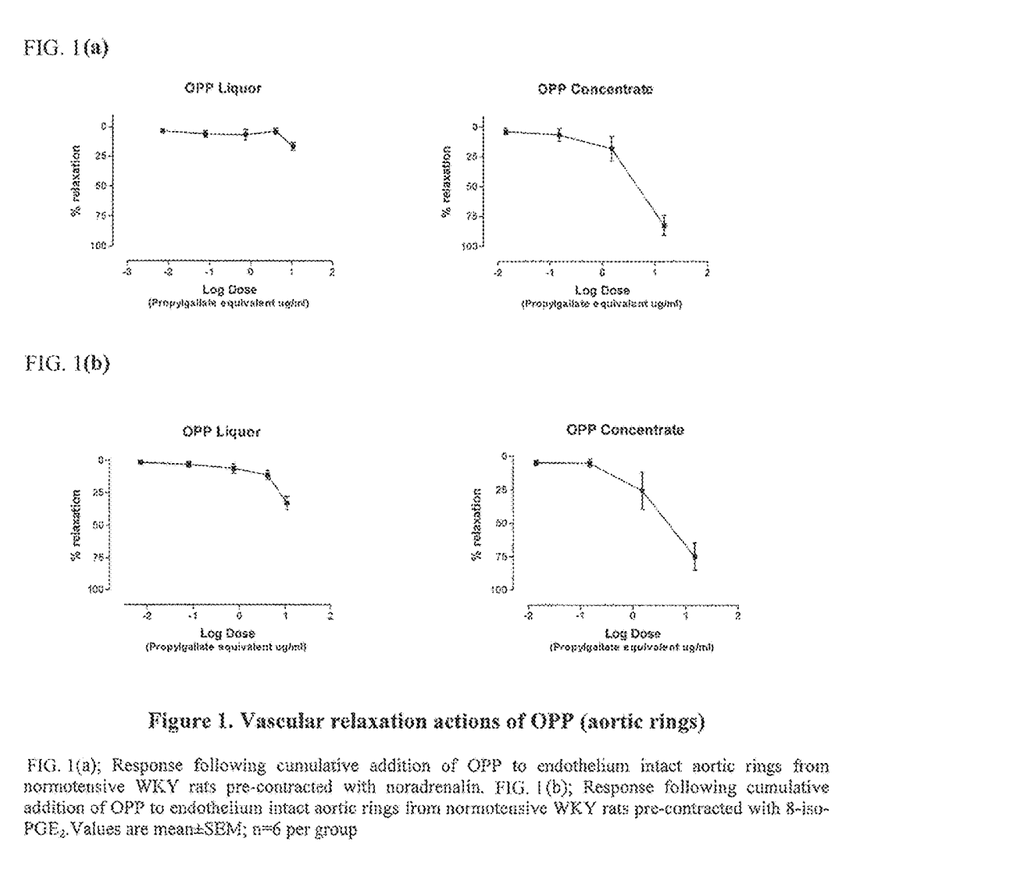
FIG. 1a-1b demonstrate the response following cumulative addition of Oil Palm Phenolic (OPP) extract to endothelium intact aortic rings from normotensive WKY rats pre-contracted with noradrenalin and response following cumulative addition of OPP to endothelium intact aortic rings from normotensive WKY rats pre-contracted with 8-iso-PGE$_2$, respectively in accordance with an embodiment of the present invention.

FIG. 1(a); Response following cumulative addition of OPP to endothelium intact aortic rings from normotensive WKY rats pre-contracted with noradrenalin. FIG. 1(b); Response following cumulative addition of OPP to endothelium intact aortic rings from normotensive WKY rats pre-contracted with 8-iso-PGE$_2$. Values are mean±SEM; n=6 per group Figure 2. Lack of relaxation activity of OPP in the absence of vascular endothelium Response following cumulative addition of OPP to endothelium denuded aortic rings from normotensive rats pre-contracted with noradrenalin. Values are mean±SEM; n=6 per group.

FIG. 3(a) *normotensive animals*

FIG. 3(b) *hypertensive animals*

Figure 3. Vasorelaxation responses to OPP (mesenteric vascular bed)

Figure 3A:
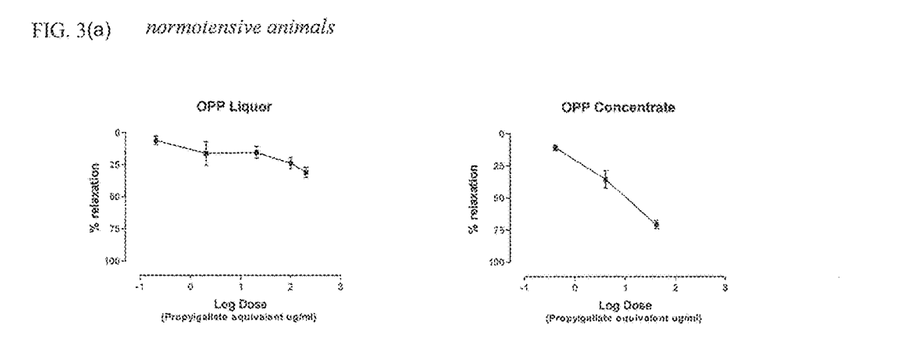
FIGS. 3a-3b are the graphs for vasorelaxation of responses to OPP (mesenteric vascular bed) in accordance with one embodiment of the present invention.
Figure 3B:
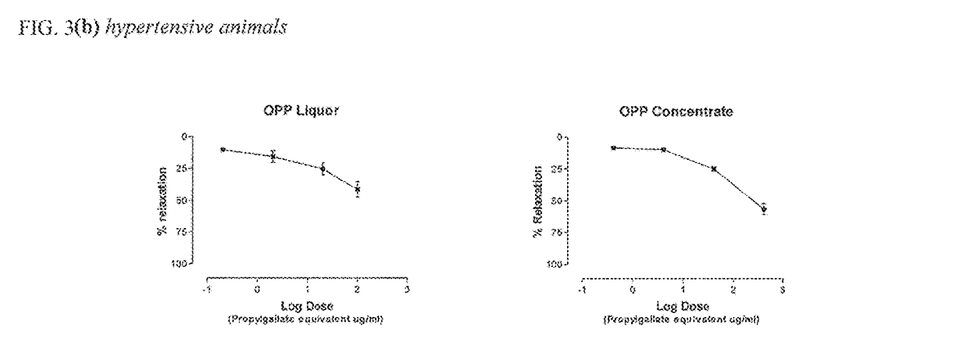

FIG. 3(a) Responses following intra luminal administration of OPP to perfused mesenteric vascular bed from normotensive rats pre-contracted with noradrenalin ($EC_{50}$). Values are mean±SEM; n=6 per group. FIG. 3(b) Responses following intra luminal administration of OPP to perfused mesenteric vascular bed from spontaneously hypertensive rats pre-contracted with noradrenalin ($EC_{50}$). Values are mean±SEM; n=6 per group

Figure 4. Reduction in blood pressure following dietary administration of OPP

FIG. 5(a) Ventricular tachycardia

FIG. 5(b) Ventricular fibrillation

Figure 5A:
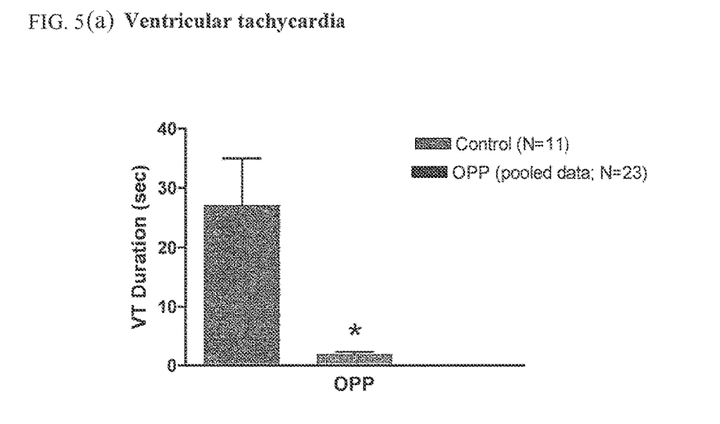
FIGS. 5a-5b provide a panel of two graphs for the pooled data (all test samples resulted in similar outcome) of protective effects of OPP against ischemia induced VT and VF.
Figure 5B:
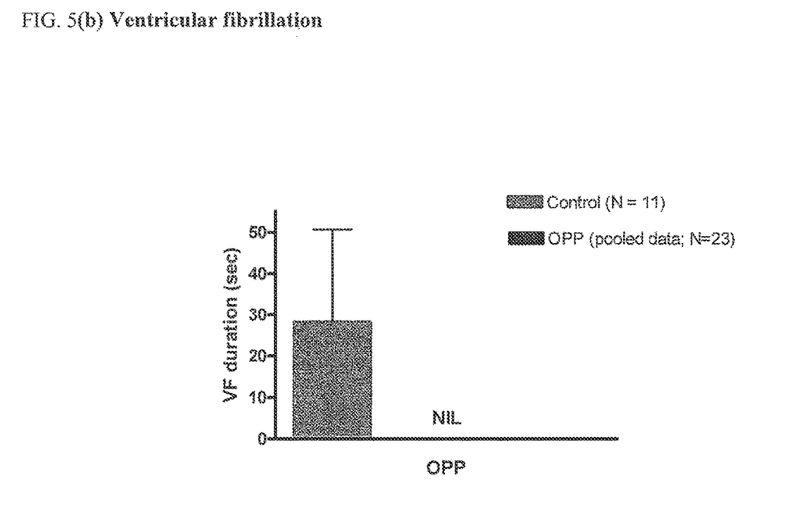

Figure 5. Protective effects of intravenously administered OPP against ischemia induced VT and VF FIG. 6(a) Ventricular tachycardia (duration)

FIG. 6(b) Ventricular fibrillation (duration)

Figure 6A:
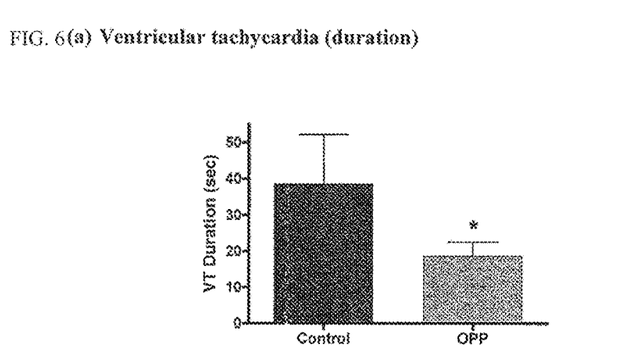
FIGS. 6a-6b provide a panel of two graphs for cardio-protective actions of OPP following 12 week dietary administration.
Figure 6B:
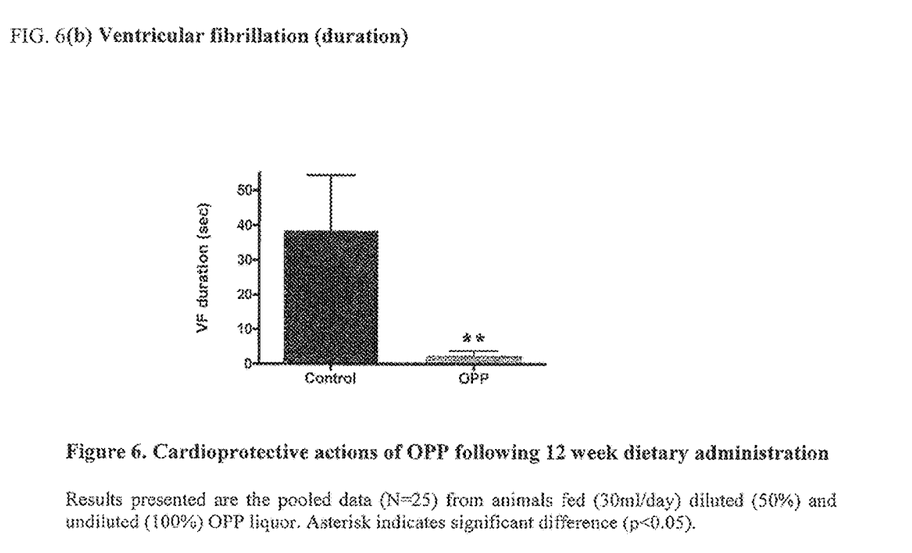

Figure 6. Cardioprotective actions of OPP following 12 week dietary administration Results presented are the pooled data (N=25) from animals fed (30ml/day) diluted (50%) and undiluted (100%) OPP liquor. Asterisk indicates significant difference ($p<0.05$).

Figure 7:
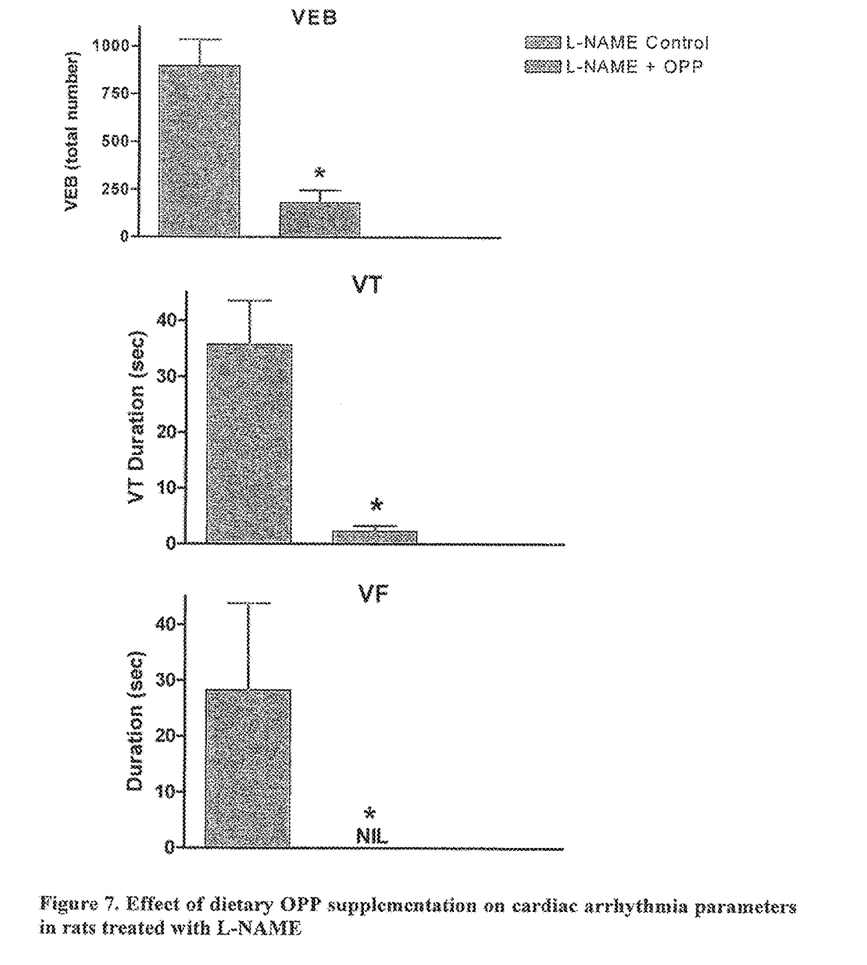
FIG. 7 provides a panel of three graphs for effect of dietary OPP supplementation on cardiac arrhythmia parameters in rats treated with L-NAME.

Figure 7. Effect of dietary OPP supplementation on cardiac arrhythmia parameters in rats treated with L-NAME VEB, ventricular ectopic beats; VT, ventricular tachycardia; VF, ventricular fibrillation. Rats were treated with L-NAME in drinking water (40mg/Kg body weight) with or without polyphenols for 5 weeks. After 5 weeks the L-NAME was withdrawn and animals were maintained on OPP (30ml/rat/day) for further 5 weeks period before subjecting to coronary artery ligation.; Control n=13; OPP n=9; Asterisk denotes significant difference $p<0.05$

COMPOSITION AND METHOD FOR IMPROVING VASCULAR HEALTH

FIELD OF INVENTION

The present invention relates to a composition comprising a botanical extract of oil palm vegetation liquor, and more particularly this invention relates to use of said composition for improving vascular health including treating and preventing vascular diseases and diseases related thereto.

BACKGROUND OF THE INVENTION

The ripe oil palm fruit bunch (*Elaeis guineensis*) used in the extraction of palm oil boasts a rich mix of deep colours (maroon, red, orange and yellow) which are indicative of an abundance of phenolics, carotenes and related phytochemicals. Indeed, palm carotenes (rich in α-and β-carotenes) and palm vitamin E enriched in tocotrienols reside in the mesocarp and are recovered from extracted crude palm oil. These products are currently available commercially.

The extraction of oil from the palm fruit results in a large aqueous stream of vegetation liquor which is currently under-utilized. This aqueous stream accounts for twice the tonnage of crude palm oil production.

In contrast to lipid-soluble compounds present in the oil phase, the aqueous stream of vegetation liquor that originates in the milling process and extraction of oil has been identified as a rich source of water soluble phenolic compounds. It has been found that the water soluble phytochemicals rich in phenolics, are extracted into the sterilizer condensate and other aqueous streams of the milling process. The use of high temperatures for the sterilisation of palm fruit bunch also inactivates the polyphenol-oxidases and preserves the phenolics.

U.S. Pat. No. 7,387,802 discloses a method for extracting a water soluble fraction using centrifuging and membrane filtration to exclude oleaginous, water insoluble and colloidal components as well as components above 41000 daltons molecular weight. This extract was identified as being rich in antioxidant phytochemicals such as phenolics and hydroxy acids. It was suggested that the extract could be used as edible products, drinks, tonics, health supplements, antioxidants and in medicinal preparations but no details of these uses are given.

It is an object of this invention to find specific uses for this product.

SUMMARY OF INVENTION

The present invention is directed to a composition for use in promoting cardio vascular health which consists of a water soluble extract having components with molecular weights below 41,000 daltons obtained from vegetation liquor of a palm oil milling process.

In one embodiment the present invention provides a composition for use in the treatment and/or prophylaxis of cardio-vascular disease which consists of a water soluble extract having components with molecular weights below 41,000 daltons obtained from vegetation liquor of a palm oil milling process.

In one embodiment, the composition may be a pharmaceutical and/or veterinary composition.

In another embodiment the present invention provides a food ingredient for promoting cardio-vascular health and protecting against cardio vascular disease which consists of a water soluble extract having components with molecular weights below 41,000 daltons obtained from vegetation liquor of a palm oil milling process.

In a further embodiment the present invention provides a method for promoting cardio-vascular health in humans and animals by administering an effective dose of a water soluble extract having components with molecular weights below 41,000 daltons obtained from vegetation liquor of a palm oil milling process.

In a further embodiment the present invention provides a method for treatment and/or prophylaxis of cardio-vascular disease in humans and animals by administering an effective dose of a water soluble extract having components with molecular weights below 41,000 daltons obtained from vegetation liquor of a palm oil milling process.

In a further embodiment the present invention provides use of a water soluble extract having components with molecular weights below 41,000 daltons obtained from vegetation liquor of a palm oil milling process.

In a further embodiment the present invention provides use of a water soluble extract having components with molecular weights below 41,000 daltons obtained from vegetation liquor of a palm oil milling process in the treatment and/or prophylaxis of cardio-vascular disease in a human and animal.

In a further embodiment the present invention provides the use of a water soluble extract having components with molecular weights below 41,000 daltons obtained from vegetation liquor of a palm oil milling process in the manufacture of a medicament for promoting vascular health in a human and animal.

In a further embodiment the present invention provides the use of a water soluble extract having components with molecular weights below 41,000 daltons obtained from vegetation liquor of a palm oil milling process in the manufacture of a medicament for the treatment and/or prophylaxis of cardio-vascular disease in a human and animal.

The cardio-vascular disease referred to above may include high blood pressure, (hypertension), coronary heart disease or widely known as heart attack, cardiovascular diseases (CVD), cerebrovascular disease (stroke), angina (chest pain), heart failure, peripheral arterial disease, artheroscle-rosis, cardiac arrythmias and rheumatic heart disease amongst others.

The extracts referred to above may be used to improve vascular integrity thus limiting adherence of cells and build up of fatty plaques, inducing vasodilatation, reducing overall oxidative burden, limiting and thus inhibiting the oxidation of LDL cholesterol, inhibiting atheroma formation, lowering blood pressure, reducing cardiac and vascular hypertrophy, improving renal function, providing cardioprotective effect, preventing atherogenesis, and maintaining heart rhythm at normal rate in the event that the blood flow is impaired or disrupted.

BRIEF DESCRIPTION OF THE DRAWINGS

This invention will be described by way of non-limiting embodiments of the present invention, with reference to the accompanying drawings, in which.

DETAILED DESCRIPTION

In line with the above summary, the disclosed description and examples relates to a composition, use and method thereof for promoting cardio-vascular health and treatment and/or prophylaxis of a cardiovascular disease (CVD) using a water soluble extract from the vegetation liquor of the palm oil milling process.

In addition to direct use of an extract, it is also possible to use different purified fractions of the oil palm phenolic extract.

The biologically active extracts of palm vegetation liquor useful in this invention are those obtained from the vegetation liquor of the palm oil milling process according but not confined to the methods disclosed in U.S. Pat. No. 7,387,802.

Although the extract contains a variety of compounds including phenolic compounds, fruit acids, fruit sugars and glycerol, for purposes of standardization the concentrations of the extracts used were measured in terms of phenolic content i.e gallic acid equivalent.

Content of Phenolic Compounds in Oil Palm Phenolic (OPP) Extract

100 μl of OPP extract was mixed with 0.2 ml Folin-Ciocalteau reagent (Sigma), 2 ml of H$_2$O, and one ml of 15% Na$_2$CO$_3$ and the absorbance was measured at 765 nm after 2 h incubation at room temperature. A standard curve was plotted with different concentrations of gallic acid and the total phenolic acid content expressed as gallic acid equivalent (GAE).

Accordingly, two strengths of OPP were used in the vascular experimental studies herein:
1) OPP (liquid) at 1,050 parts per million (ppm)
2) OPP concentrate prepared in the form of freeze dried concentrate of OPP-30,000 ppm, GAE Vascular Relaxation Generally, the elevation of total peripheral vascular resistance or also known as systemic resistance in hypertension is primarily due to changes in structural properties of the blood vessels (vascular remodeling and/or hypertrophy) and the functional state; increased vascular tone arising from an unbalanced or impairment of the vasoconstrictor and vasodilator systems. It is also known that the changes in the balance between sympathetic vasoconstriction and endothelium-dependant vascular relaxation, mediated primarily via nitric oxide (NO), can influence the regulation and maintenance of normal blood pressure (BP). Such changes also form the basis for elevation in BP in several forms of experimental hypertension.

A number of studies have reported that dietary polyphenols may influence vascular function and influence blood pressure in several experimental models of hypertension.

Methods for studying the functional properties of larger (conductance) vessels for the purpose of the present invention include the aortic ring preparation, which is known in the art as a common and reliable method for in vitro experimental technique. This method was used for the assessment of the potential vasodilatory effects, which include the assessment of the role of vascular endothelium and the possible mode of actions thereof. Another significant aim of using the method was to investigate and thus determine the association between modifications in vascular reactivity or compliance in larger vessels (stiffness/elasticity) and vascular flow characteristics.

Methods for studying the blood pressure regulation and in hypertension for the purpose of the present invention include the study on mesenteric vascular bed. The imperative indications relative to measuring or analyzing blood pressure regulation and hypertension can be observed via the systemic vascular resistance. The vascular resistance is defined in the art as the resistance to flow that needs or must be overcome in order to provide blood within the organ system. As the mesenteric vascular bed is known in the art as a significant contributor to systemic vascular resistance and compared to larger vessels such as aorta, contractions of smaller arteries are more relevant to blood pressure analysis. It is known that both an increased cardiac output and increased vascular resistance in peripheral circulation can lead to hypertension.

Comprehendingly, in order to determine the effect of OPP in vascular resistance, tissue preparations which measure vascular function in resistance vessels is therefore selected, hence the perfused mesenteric vascular bed study. In the perfused mesenteric preparation for the present invention, the changes in intra-luminal pressure development due to the constriction of resistance arteries (peripheral circulation) are measured.

It is further known that agents that influence total peripheral resistance via vasorelaxation are considered beneficial, as functional studies have demonstrated that anti-hypertensive therapy increase blood flow, decrease vascular resistance and modify structural vascular alterations both in experimental animal models and in humans.

The effect of OPP of the present invention in vascular resistance were observed and results show that OPP exerts strong endothelium-dependant vascular relaxation in isolated vascular preparations, as depicted in FIG. 1a-1b, and FIG. 2a-2b.

The present invention will now be described by way of example only, the invention is not to be limited to the discussion of the examples below:

Materials and Methods:

Oil Palm Phenolics (OPP) obtained through a patented process (U.S. Pat. No. 7,387,802) were used in these studies. The concentration of OPP in the extract was determined using the Folin-Ciocalteu assay Folin Ciocalteu reagent was mixed with serial dilutions of test extracts and gallic acid standards, and incubated for 15 mins. Sodium carbonate (1.9 mol/L) was added, mixture vortexed and incubated for 60 mins. The absorbance (765 nm) was read against gallic acid standards. Results were expressed as gallic acid equivalents (GAE).

EXAMPLE 1

Aortic Ring Preparation

Wista-Kyoto (WKY) rats were used for to determine the effect of OPP on vascular functions.

Isolated segments (3 mm) of thoracic aorta from normotensive Wistar-Kyoto (WKY) rats (12-14 weeks old) were mounted under isometric conditions in organ bath chambers. In some rings the endothelium was removed by careful rubbing of the intima with a moistened cotton swab. The tissues equilibrated for at least 60 minutes before contracting with KCl (20 mmol/L) to test tissue viability. The change in tension was monitored by a computer based data acquisition system. The rings were pre-contracted with half-maximal ($EC_{50}$) dose of noradrenalin (NA) or isoprostaneE$_2$ (8-isoprostaglandinE$_2$). Test extracts were dissolved and diluted serially with buffer and added in cumulatively, directly to the bath. The change in tension recorded and the extent of relaxation calculated.

Results

FIG. 1a-FIG. 1b plot the response following accumulative addition of OPP to endothelium intact aortic rings from normotensive WKY rats pre-contracted with noradrenalin (NA). It is observed from the graphs that OPP caused dose-dependant relaxation in aortic rings pre-contracted with either noradrenalin or 8-iso-PGE$_2$.

Results obtained were accordingly recorded and plotted as seen in FIG. 1a-FIG. 1b for OPP liquid and freeze-dried OPP preparation respectively.

As shown in FIG. 1a and FIG. 1b OPP liquid showed lower potency compared to that of the freeze-dried OPP preparation. Subject to the extent of concentration of the active ingredient, it is observed that the freeze-dried OPP preparation caused substantial vasorelaxation activity that was therefore considered dose-dependant. It is eminent from the graph that the freeze-dried OPP preparation caused approximately over 75% relaxation at the highest dose tested. It would be appreciated by a person skilled in the art that from the results it is further observed that the relaxation profile and the maximum level exerted by freeze-dried OPP preparation were similar to those observed with the pharmacological agent acetylcholine, an established vascular relaxant.

Figure 2:
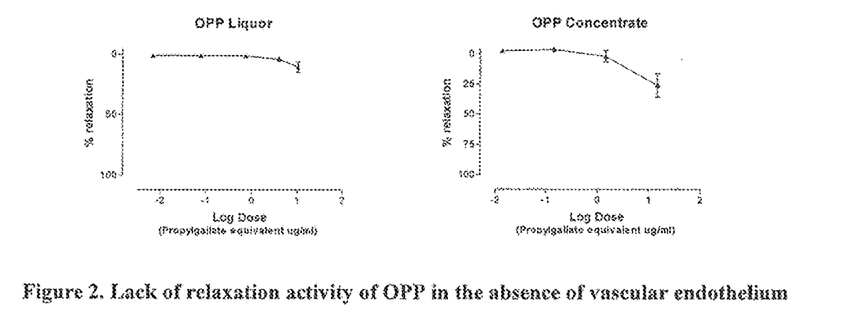
FIG. 2 illustrates lack of relaxation activity of OPP in the absence of vascular endothelium.

FIG. 2 plots the response following the cumulative addition of OPP to endothelium denuded aortic rings from normotensive rats pre-contracted with noradrenalin. It is observed from the said graph that there was lack of relaxation activity of OPP in the absence of vascular endothelium denuded ring, therefore suggesting OPP promotes vasodilation via endothelium derived nitric oxide related mechanism.

EXAMPLE 2

Mesenteric Vascular Bed Test

Blood vessel preparations are from spontaneously hypertensive rats (SHR), which have impaired vasorelaxation and do not respond effectively to several pharmacological agents including acetylcholine.

The superior mesentery artery was cannulated and flushed with heparin-saline. The entire mesenteric bed, including the intestinal tract was removed, and the gut content was removed by flushing with saline. The preparation was mounted in a 50 ml organ bath chamber and continuously perfused with oxygenated Krebs-Henseleit medium. After 30 min. of equilibration, tissue viability was assessed by cumulative intra-luminal injection of various agonists (KCl, NA). The pressure was raised by the addition of NA ($EC_{50}$) in the bath perfusate.

Vasorelaxation responses to the pharmacological agent acetylcholine (ACh) and OPP were determined by measuring the extent of pressure reduction following intra luminal administration. The pressure changes were monitored using MLT844 Physiological Pressure Transducer connected to a pressure amplifier (DA100C, BIOPAC Systems Inc.) and a computer based data acquisition system (MP100WSW High performance data acquisition unit, BIOPAC Systems Inc.)

Results

Results obtained were accordingly recorded and plotted as seen in FIG. 3a-3b.

FIGS. 3a-3b demonstrate the results for the mesenteric vascular bed study, whereby there is provided the responses following intra luminal administration of OPP to perfused mesenteric vascular bed from normotensive (normal blood pressure) rats pre-contracted with noradrenalin ($EC_{50}$) and responses following intra luminal administration of OPP to prefused mesenteric vascular bed from spontaneously hypertensive (high blood pressure) rats pre-contracted with noradrenalin ($EC_{50}$) respectively. The graphs indicate induced relaxation in the resistance blood vessels (mesenteric vascular bed) for both animals, whereby it is observed that intra luminal administration of OPP caused relaxation in vessels of the normotensive and hypertensive animals. Accordingly, OPP has shown efficacy in causing over 70% relaxation at the highest dose tested.

Blood Pressure Lowering

In regulating blood pressure (BP), nitric oxide (NO) serves the main function of inducing vasodilation by way of diffusing across the endothelium into the adjacent smooth muscle, and thus causing the said smooth muscle to dilate. It is produced from L-arginine, upon stimulation, with the assistance of a catalyst, the endothelial nitric oxide synthase (eNOS). Understandably, reduced amount of NO will result to hypertension.

In order to determine the effect of OPP in blood pressure reduction, a method utilizing a nitric oxide (NO) deficient model of hypertension was used. This animal model involves the inhibition of endogenous NO production with L-NAME ($N^G$-nitro-L-arginine methyl ester) that leads to elevation in BP.

The present invention provides positive results in blood pressure lowering study which will be described and thus understood by reference to the examples herein.

EXAMPLE 3

Blood Pressure Study

Dietary Feeding 12 weeks old Sprague-Dawley rats were fed a standard laboratory rat diet, formulated to contain low n-3 polyunsaturated fatty acids (Glen Forrest Stock feeders, Glen Forrest, W.A., Australia). The OPP was provided as a drink at a rate of 30 ml/rat/day. OPP were provided at two different strengths-as liquid (1500 GAE) and in a concentrated liquid form at 3000 GAE (prepared using the freeze-dried preparation at 30,000 GAE). Rats were pre-treated for four weeks prior to challenge with L-NAME. To minimise any adverse effect due to sudden exposure to L-NAME, in the first two weeks rats were maintained at a 10 mg/Kg before increasing the dose to 15 mg/Kg and maintained at this level for the next 6 weeks along with OPP. The four experimental groups included (1) control (2) L-NAME (3) L-NAME+OPP liquid and (4) L-NAME+OPP liquid concentrate. The intakes were adjusted every two days to allow for gain in bodyweight.

Blood Pressure Monitoring

BP was monitored fortnightly by standard photoelectric tail-cuff procedure (IITC, Life Sciences, Woodlands Hills, Calif., USA) as described in detail previously. Briefly, rats (pre-trained) were placed, in restraining tubes (IITC Life Sciences model 805 and model 815) and the tails were occluded with an appropriate sized cuff coupled to a pneumatic pulse transducer and electrophysiograph (IITC model 65-12). The pulse was detected as the cuff pressure was reduced and the pressure at which the first pulse detected was taken as the systolic blood pressure and computed automatically (IITC software package). The ambient temperature was carefully controlled (30° C.) and the average of 3-4 readings was taken as the final reading.

Results

Figure 4A:
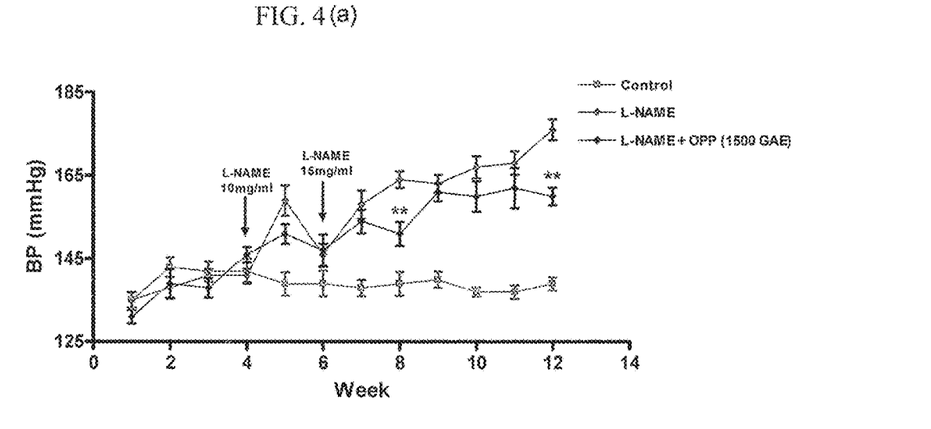
FIGS. 4a-4b are the graphs showing the reduction in blood pressure following dietary administration of OPP in accordance with another embodiment of the present invention.
Figure 4B:
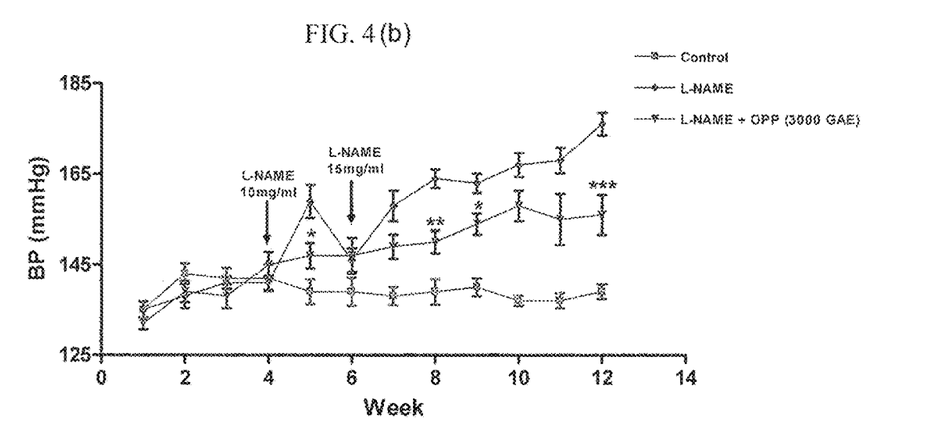

Results obtained were accordingly recorded and plotted as seen in FIG. 4a-4b.

It is noted that in this study, rats were pre-treated for 4 weeks with OPP before treatment with N-nitro L-arginine methylester (L-NAME), an antagonist of L-arginine. The main objective of the said pre-treatment with L-NAME is to elevate the blood pressure of the rats.

FIG. 4a indicates that the introduction of L-NAME (10 mg/Kg) resulted in a sharp rise in BP (18 mmHg) in the L-NAME control group. However, such initial rise was not observed ($p<0.05$) in the rats that received OPP. The increase in L-NAME dosage to 15 mg/Kg as shown in the graph continued to result in a gradual increase in BP during the course of the treatment period. This observation is in contrast to the untreated control group; whereby the L-NAME treated (15 mg/Kg) rats displayed significantly higher blood pressure values throughout the duration of the experiment.

It is evident from the plotted graphs that the rats supplemented with OPP showed retardation in blood pressure development when compared to the L-NAME treated group. This was more clearly apparent in the OPP concentrate fed animals which received a higher amount or dose of extract. Referring to FIG. 4b, the animals in this group demonstrated more stable BP values throughout the experiment. The final BP values (mmHg) at the conclusion of the experiment were-untreated control 139±1.6; L-NAME (control) 176±2.5; OPP liquid 160±2.1 OPP liquid concentrate 156±4.4* ($p<0.01$, *$p<0.001$, n=12 per group).

The results have therefore indicated that OPP has significant effect on the blood pressure system and thus reducing elevated blood pressure in. In addition, oral administration of OPP lowered the blood pressure in a NO-deficient model of hypertension in dose-related manner. In can be further highlighted that in view of OPP providing antioxidant properties, the blood pressure may be lowered by way of scavenging the elevated amount of ROS and thus reducing or inhibiting oxidant stress which in most cases, may lead to hypertension or atherosclerosis.

Cardioprotection

In another embodiment of the present invention, the OPP of the present invention were found to demonstrate protective actions, whereby the said protective actions including protection against the oxidation of low density lipoprotein (LDL) and thus the development of atherosclerosis, protection against ischemia induced ventricular tachycardia (VT), ventricular fibrillation (VF) and sudden cardiac death (SCD).

Generally, the VT incidence and VF data are often associated with the occurrence of sudden cardiac death; therefore it is highly essential that these data are quantified within a region.

The following study was designed to evaluate the cardioprotective actions of OPP as mentioned in the preceding paragraph, whereby the obtained results will be described shortly herein.

EXAMPLE 4

Protective Effects of OPP Following Acute (Intravenous) Administration

Twelve-week old male normotensive (WKY) rats were fed a standard laboratory rat diet formulated to contain low n-3 polyunsaturated fatty acids (Glen Forrest Stockfeeders, Glen Forrest, Western Australia). The total fat (w/w) content was increased to 10% (w/w) using lard. The base diet contained no fish meal as a protein source, thereby minimising the possible presence of long chain n-3PUFAs. Previous experience in this laboratory has demonstrated that pro-arrhythmic effects of lard may be counteracted by the presence of fish meal in the base diet. The animals were maintained on this diet for a period of three months before experimentation. It has previously been demonstrated that both the age and the type of fat in the diet are key determinants of arrhythmic vulnerability.

EXAMPLE 5

Protective Effects of OPP Following Dietary Feeding

Male WKY rats aged 12 weeks of age (Animal Resource Centre, Western Australia) were housed in groups of 6 and randomly allocated to different experimental groups. Bodyweights were recorded fortnightly throughout the experiment. Animals were provided with ad libitum access to food and water and were maintained under a 12/12 light/dark cycle. They were fed a diet as described above (study 1) and the OPP was provided as a drink at a rate of 30 ml/day, and replenished thrice weekly. The OPP was kept frozen in individual 1 litre bottles and thawed prior to use. Two dose levels—undiluted (100% OPP i.e 1050 ppm GAE), and after 1:1 (v/v) dilution with Milli Q water (50% OPP)—were used. Supplementary water was provided as required to individual cages when the test compounds had been consumed. The duration of intervention was 3 months. Bodyweights were recorded fortnightly, and animals were monitored routinely for overall health and well being.

EXAMPLE 6

Protective Effects Following OPP Feeding in a Nitric Oxide Deficient Model 12-week old WKY rats were treated with L-NAME ($N^G$-nitro-L-arginine methyl ester; 40 mg/kg bodyweight) for 5 weeks in the absence (water control) or presence of OPP. The intakes were adjusted every two days to allow for gain in bodyweights. Undiluted OPP liquid (1500 GAF) was provided (30 ml/rat/day) throughout the experiment. After the withdrawal of L-NAME at 5 weeks, the animals continued on their dietary OPP treatment for further 5 weeks before subjecting to coronary artery ligation as described below.

EXAMPLE 7

Coronary Artery Ligation

Myocardial ischemia was induced by a temporary occlusion of the LAD (left anterior descending coronary artery) as described in detail previously. In brief, rats were anaesthetised (sodium pentobarbitone 60 mg/ml stock; 1.0 ml/kg, ip) and intubated. After tracheotomy, animals were ventilated with room air using a rodent ventilator (model 7025, Ugo Basile, Comerio Varese, Italy) with a stroke volume of approximately 18 ml/kg body weight and at a rate of 60 strokes per min.

The femoral artery and vein were cannulated to monitor blood pressure and for the administration of saline/drugs/test compounds as required. After left thoracotomy the heart was exteriorised from the thoracic cavity, and using an atraumatic needle (6/0 braided silk), a ligature was placed just beneath and around the LAD coronary artery. The heart was returned to the chest cavity and the animals were allowed to stabilise (5 min) prior to infusion of test compounds. For study 1, the test compounds were made in saline at a stock concentration of 100 mg/ml. The test extracts were infused at a volume of 0.1 ml/100 g body weight (a dose level of 0.1 g/kg body weight) via the femoral vein at a rate of 0.13 ml/min using an automated syringe pump (model 341B, Sage Instruments, Boston, Mass.) 30 min. prior to coronary occlusion. Regional ischemia (occlusion phase) was induced by tightening the ligature. The LAD coronary artery occlusion was maintained for period 30 min. to assess ischemia-induced arrhythmia. At the completion of the experiment, rats were exsanguinated, hearts excised and perfused with dye (Evans blue, 0.1 ml) to determine the zone at-risk.

Blood pressure (BP), heart rate (HR) and electrocardiogram (ECG) changes were monitored throughout the experimental period and recorded using a computer based data acquisition system (BioPak-MP100). Ventricular ectopic activity was assessed according to the criteria advocated on the Lambeth convention. The parameters computed include the number of ventricular ectopic beats (VEB), and the incidence and duration of ventricular tachyarrhythmia, including ventricular tachycardia (VT) and ventricular fibrillation (VF).

Statistical Analysis

It is noted that data were expressed as mean±SEM. The incidences of VT and VF were compared using the Chi-square test. Differences in the number of VEB, the duration of VT and VF between the control and individual treatments were analysed using the Mann-Whitney rank-sum test. The pooled data from concentrated samples were subjected to one way ANOVA followed by Bonferroni's post hoc test. A p value of <0.05 was considered significant. The statistical analyses were performed using the Graph Pad-In Stat (version 4.0) computer software program.

In order to determine the cardioprotective effects of the present invention in the aforementioned animal models, OPP of the present invention was prepared in the following concentrations and referred herein as Test Samples.

Test Sample 1: OPP liquid (1,050 Gallic Acid Equivalent, GAE)

Test Sample 2: 2.5 fold concentrate of the OPP liquid (2,625 GAE)

Test Sample 3: 3 fold concentrate of the OPP liquid (3,150 GAE)

Test Samples 4: 12.5 fold concentrate of the OPP liquid (13,125 GAE)

Test Samples 5: Freeze dried preparation of OPP (30,000 GAE)

OPP was assessed following intravenous administration, directly into the blood stream.

Results

Acute Administration Study

The results obtained for all studies related to cardioprotection effects of OPP will be described shortly herein.

Table 1 below provides the values as accorded for the test on the effects of different OPP concentrations on ventricular tachycardia (VT) durations.

TABLE 1

Effects of OPP on ischemia induced ventricular tachycardia (VT) in the anaesthetized rat

| Compound | N | Ventricular tachycardia (VT) | |
|---|---|---|---|
| | | Incidence (%) | Duration (sec) |
| Control (saline) | (11) | 100 | 27.0 ± 8.0 |
| Test Sample 1 (TS1) | (5) | 80 | 18.5 ± 12.8 |
| Test Sample 2 (TS2) | (9) | 33* | 1.0 ± 0.7* |
| Test Sample 3 (TS3) | (5) | 60 | 2.5 ± 1.1* |
| Test Sample 4 (TS4) | (6) | 83 | 2.8 ± 1.3* |
| Test Sample 5 (TS5) | (3) | 67 | 1.3 ± 0.8* |

Values reported are the mean ± SEM of the duration and the incidence of VT during a 30 min. occlusion period. N refers to the number of animals per group. Test compounds were infused 30 min. prior to the induction of ischemia by ligation of the left anterior descending coronary artery. Statistical significance (*) at the level of 5% or better.

As shown in Table 1 the VT incidence has reduced approximately 20% with the administration of Test Sample 1 when compared to that of the control model. A substantial reduction of VT incidence is observed when models were administered with Test Sample 2.

FIG. 5a-5b plot the pooled data (all test samples resulted in similar outcome) of protective effects of OPP against ischemia induced VT and VF, whereby as seen in the said graphs there are significant difference between the control and OPP administered animals in the VT and VF incidence.

The incidence of ventricular fibrillation (VF) in the control group was 36% (4/11). OPP Test Sample 1 (OPP liquor) was without effect against VF and this group showed similar VF incidence (40%). In contrast, none of the animals in the concentrated OPP samples (Test Samples 2-5) developed VF.

From the values tabulated in Table 1 and as summarized in FIG. 5a-5b, it is evident that OPP of the present invention demonstrates significant protection or inhibition against the % incidence and the duration of ventricular tachycardia (VT) by way of reducing the incidence and duration of VT following acute administration (intravenous) directly into the circulation. Based on these results, it is shown that OPP may provide anti-arrhythmic effect for the in vivo animal model of cardiac arrhythmia used for the purpose of the present invention.

Dietary Feeding Study

The main objective of this study is to analyse the effect of OPP on % incidence and duration of VF and mortality from VF during the 30 minutes ischemic period of rats fed OPP liquor (50% and 100% strength's) for a duration of three months.

As shown in Table 2 appended below, as opposed to the control (water) group whereby there were 3/12 deaths, treated animals showed no deaths. This therefore indicates that the OPP feeding facilitates in reducing the VF (% incidence and duration).

TABLE 2

Effects of OPP feeding on ischemia induced ventricular fibrillation (VF) in the anaesthetized rat

| Treatment | N | Ventricular Fibrillation (VF) | | |
|---|---|---|---|---|
| | | % Incidence | Duration (sec) | % Total Mortality |
| Control | 12 | 58 | 38.4 ± 15.8* | 25 (3/12) |
| OPP liquid (50%) | 13 | 23 | 4.0 ± 2.6 | 0 (0/13) |
| OPP liquid (100%) | 12 | 8# | 0.4 ± 0.4 | 0 (0/12) |

Values reported are the mean ± SEM of the duration and the incidence and mean duration of VF during a 30 min. occlusion period. N refers to the number of animals per group.
p < 0.05 (vs. control), Chi-square test.
*denotes significance difference from OPP treated groups (ANOVA; Turkey's test; P < 0.05 or better)

Table 3 appended below tabulates the pooled data recorded for effects of OPP long term dietary feeding (3 months) to animals, whereby the positive results demonstrated are summarized as FIG. 6a-6b. Results presented in FIG. 6a-6b are the pooled data (N=25) from animals fed (30 ml/day) diluted (50%) and undiluted (100%) liquid.

TABLE 3

% Incidence of VT and VF in rats fed a pro-arrhythmic diet supplemented with OPP (pooled data)

| Treatment | Incidence (%) | |
|---|---|---|
| | VT | VF |
| Control | 96 (22/23) | 91 (21/23) |
| OPP | 88 (22/25) | 52 (13/25)* |

Values reported are % incidence of VT and VF during a 30 min. occlusion period. Values in parenthesis refer to the number of animals per group. % incidence of VF in the OPP is significantly different (*p < 0.05, Chi-square test).

It is therefore observed that treating OPP to the animals via long term dietary feeding provided a significant effect on the reduction of VF and VT (incidence and duration) which are the similar effects observed following an intravenous administration to the rats.

Dietary Feeding (Nitric Oxide Deficient Model)

It is noted that in order to determine the effect of dietary administration of OPP on the vulnerability to cardiac arrhythmia, the rats were treated with L-NAME. The rationale for this was based on the premise that OPP may be able to exert cardioprotection by promoting the availability of nitric oxide (NO) in this NO-deficient model. It has been reported that impaired production/availability of NO is pivotal to the cardiovascular abnormalities observed in this model.

At the end of this study, the administration of OPP demonstrated cardioprotection effect similar to that observed with untreated animals fed a pro-arrhythmic diet and as plotted in FIG. 6a-6b.

Therefore, FIG. 7 shows that OPP feeding resulted in considerable cardioprotection in the NO-deficient model. For instance, it is evident from the results that the total number of VEB was reduced (p<0.05) in the OPP supplemented group compared to the control rats and was also reflected in the extent of VT incidences since compared to 100% incidence (13/13 animals) in the control group, OPP group displayed only 55% (5 out of 9). This protection by OPP against % VT (p<0.05, Chi-square test) was also apparent when the duration of VT activity was compared. In addition, the OPP feeding led to a significantly shortened duration (seconds) of VT (control 35.7±7.8; OPP 2.3±1.0*, p<0.05).

Conclusively, based on the results obtained it is evident that OPP provides considerable protection against ischemia induced cardiac arrhythmias (VEB, VT), ventricular fibrillation and sudden cardiac death. Accordingly, the results obtained from the said studies verifies the observations made with the concentrated OPP test samples in an acute setting following administration directly into the blood stream as seen in Table 1 and FIG. 5.

Atherosclerosis

In numerous plant extract studies, several results obtained have shown atherogenesis prevention, whereby it was found that the compounds were able to decrease the susceptibility of low density lipoprotein (LDL) to lipid oxidation and retard the development of atherosclresosis in animal model such as rabbits fed pro-atherogenic diet.

A study was conducted to determine another embodiment of the present invention, the protective effects of OPP against in vito oxidation of human LDL and the development of athrematous lesions in the rabbit model of atherosclerosis. Results from this study were accordingly recorded and plotted in Tables 4-6.

EXAMPLE 8

Inhibition of LDL Oxidation by OPP
Materials and Methods

Oil Palm Phenolics (OPP) obtained through a patented process (U.S. Pat. No. 7,387,802) were used in these studies. The concentration of OPP in the extract was determined using the Folin-Ciocalteu assay. Folin Ciocalteu reagent was mixed with serial dilutions of test extracts and gallic acid standards, and incubated for 15 mins. Sodium carbonate (1.9 mol/L) was added, mixture vortexed and incubated for 60 mins. The absorbance (765 nm) was read against gallic acid standards. Results were expressed as gallic acid equivalents (GAE).

Plasma LDL Isolation

Blood from six healthy normocholesterolemic adult volunteers was collected into vacutainer tubes containing EDTA and centrifuged (1000× g for 15 min) to isolate plasma. LDL was isolated by density gradient centrifugation in a Beckman Ultracentrifuge using a 50.2 Ti rotor, based on the method of Sundram et al. (2). The LDL layer following sequential isolation at density 1.063 kg/L was removed and dialyzed against 4 L of PBS, pH 7.4 and purged with nitrogen for 12-18 h. After dialysis, the cholesterol concentration in the pooled LDL sample was determined using an automated Cholesterol assay. The LDL fraction was used immediately or immediately stored under nitrogen at 4° C. and analyzed for LDL oxidation within 48 h.

Copper-Mediated LDL Oxidation

To evaluate the ability of OPP to inhibit copper (Cu) mediated LDL oxidation, conjugated dienes (CD) were continually monitored at 5-min intervals at 37° C. by UV absorption at 234 nm. LDL oxidation was initiated by addition of copper sulfate at a final concentration of 6 µmol/L to 90 µg of LDL cholesterol in a final volume of 1 mL. The purified test compounds (catechin obtained from Sigma Chemical) and OPP extracts were added immediately before the addition of the oxidant. The extracts were added at a final concentration range of 0.25-1.0 µmol/L GAE and the purified compounds at a final concentration of 0.25 or 0.5 µmol/L. All LDL oxidations were performed in triplicate. The lag time in the presence or absence of the test compounds was determined as the intercept of the slopes for the lag and propagation phases. This was compared with the control oxidized LDL to determine the percentage of LDL oxidation inhibition.

Oxidation of LDL initiated by Cu ions and conjugated diene (CD) formation was measured at 234 nm. Extracts at concentrations of 0.25, 0.5 and 1.0 µmol/L GAE inhibited Cu mediated LDL oxidation in a dose-dependent manner since LDL lag phase was lengthened up to 10%, 53% and 81%, respectively, relative to the control LDL. Purified catechin was used as control phenolic compounds and compared with control LDL. The highest concentration of catechin (0.5 umol/L) resulted in 55% increases in lag time with Cu-mediated oxidation system.

TABLE 4

Effect of oil palm phenolics (OPP) and pure catechin on conjugated diene (CD) formation lag time

| Oil Palm Phenolics | Lag time (mins) |
|---|---|
| 0.25 µmol/L | 74 ± 9 |
| 0.5 µmol/L | 103 ± 14* |
| 1.0 µmol/L | 121 ± 7* |
| LDL - control | 67 ± 12* |
| Catechin 0.25 µmol/L | 87 ± 13 |
| 0.5 µmol/L | 104 ± 10 |

Three concentrations of palm phenolics (0.25, 0.5 and 1.0 umol/L) were compared against control LDL through copper mediated LDL oxidation.
Values are means ± SD; n = 6 LDL preparations. All oxidations were conducted in triplicate and averaged for each LDL preparation.
*Significantly different from control LDL, $p < 0.05$

EXAMPLE 9

Rabbit Arthrosclerosis Study

Twenty-four New Zealand White rabbits were divided into three groups of 8 and fed an atherogenic diet for 100 days. The diet contained 35% energy from fat, with added cholesterol 0.15% (w/w). The fat comprised 67.1% saturated fatty acids, primarily as C12:0+C14:0 (Table 5). Group 1; the Control group (CTR) was fed the atherogenic diet, and was provided distilled water as their drinking water. Two concentrations of OPP were tested in two groups of 8 animals each and these were fed the atherogenic diet and palm phenolics (at a concentration of 500 mg gallic acid equivalents/L (mg GAE/L)) or 1000 mg GAE/L was provided as drinking fluid; Groups 2 and 3 respectively.

TABLE 5

Fatty acid composition (%) of atherogenic fat blend used to prepare diets

| Carbon No. | Blended Oil |
|---|---|
| SFA | 67.14 |
| 12:0 | 40.38 |
| 14:0 | 14.50 |
| 16:0 | 9.72 |
| 18:0 | 2.40 |
| 20:0 | 0.14 |
| PUFA | 12.02 |
| 18:2(n-6) | 11.88 |
| 18:3(n-3) | 0.14 |
| MUFA | 15.68 |
| 18:1(n-9) | 15.68 |

SFA—saturated fatty acids; PUFA—polyunsaturated fatty acids; MUFA—monounsaturated fatty acids. The test diet contained 40% energy from fat with 0.15% added cholesterol.

Animals were fed diets ad libitum and had free access to drinking fluids. Fasting blood was obtained prior to sacrifice and plasma total cholesterol (TC), high density lipoprotein-cholesterol (HDL-C), low density lipoprotein-cholesterol (LDL-C) and triglycerides (TG) were analyzed. At the end of the 100 days supplementation, the rabbits were killed by a lethal injection of Nembutal and the entire aorta was traced, dissected and fixed in 10% formalin. The said aortas were then stained with Oil Red-O which resulted to the lipid deposits in the aorta to be stained red thus delineation of atheromatous deposits in the intima and lesions were quantified using a digital image analysis system. It is noted that the intensity of staining was directly proportional to the amount of the lipid deposits. Aortic lesions were scored both visibly and on the basis of the intensity of lipid stains recorded by the said digital image analysis system. Means were calculated and a final score assigned to the control and experimental groups. These observations were further verified by plasma and aortic lipid analyses.

Table 6 shows the results for the effect of OPP on atherosclerosis. It is observed that the lipid profile analysis in all the experimental groups did not show any significant differences. Fibrous plaques (% of total aorta area) were detected in the CTR group (7.96±4.82) but were significantly reduced in OPP supplemented groups (OPP-500 mg GAE/L 1.41±4.45 units????) groups. Similar outcomes were observed for fatty plaques.

The results obtained indicate that compared to the control group, the provision of OPP provided significant protective effect in a dose-dependent against the development of atherosclerotic lesions in this animal model. It is noteworthy that this protection was achieved against a pro-atherogenic high-fat background diet.

TABLE 6

Effect of experimental diets on the development of aortic lesions in the rabbit model of atherosclerosis

| Parameter | CTR | OPP-500 | OPP-1000 |
|---|---|---|---|
| Fibrous Plaque | 7.96 ± 3.82$^{ab}$ | 1.41 ± 0.81$^{ad}$ | 0.96 ± 0.45$^{b}$ |
| Fatty Plaque | 8.53 ± 3.47$^{ab}$ | 4.82 ± 2.66$^{a}$ | 3.49 ± 2.98$^{ab}$ |
| Fatty Streak | 12.41 ± 5.02$^{ab}$ | 10.28 ± 5.74$^{ac}$ | 6.45 ± 3.72$^{bc}$ |

TABLE 6-continued

Effect of experimental diets on the development of aortic
lesions in the rabbit model of atherosclerosis

| Parameter | CTR | OPP-500 | OPP-1000 |
|---|---|---|---|
| Lesion Free | 70.93 ± 6.76$^{ab}$ | 83.40 ± 8.04$^a$ | 87.92 ± 8.12$^{ab}$ |
| Total Area (%) | 99.83 ± 0.28 | 99.97 ± 0.16 | 99.85 ± 0.27 |
| Total Area (mm) | 1390.8 ± 109.2 | 1436.8 ± 128.9 | 1453.8 ± 127.7 |

Values are % of total aorta area (mm); n = 9 animals per group and presented as means ± SD. Means with common superscript are significantly different (p ≤ 0.05). Total plasma cholesterol was >15 mmol/dL in all groups. LDL and HDL levels were not significant among groups in this cholesterol driven atherosclerosis model.
CTR - Control group provided drinking water without any antioxidants added, water soluble OPP (oil palm phytochemicals) at 500 or 1000 mgGAE/L and provided mixed in the drinking water of these animals.
Fibrous Plaque - Raised nodular lesions, continuous, intense red, white hard and visible to naked eyes
Fatty Plaque - Raised distinct lesions, intensely stained red
Fatty streak - Lipid accumulation, stained light red
Lesion Free - Healthy intima Dosage and Formulation Generally, the composition comprising OPP may be prepared in various suitable forms for direct or oral administration for improving vascular heath, treating and preventing vascular diseases and diseases related thereto.

The compositions of the invention include those suitable for oral, rectal, optical, buccal (for example, sublingual), parenteral (for example, subcutaneous, intramuscular, intradermal and intravenous) and transdermal administration. The most suitable route in any given case will depend on the nature and severity of the condition being treated and the state of the patient, Compositions suitable for oral administration may be presented in discrete units, such as capsules, sachets, lozenges, or tablets, each containing a pre-determined amount of the extract: as a powder or granules; as a solution or a suspension in an aqueous or non-aqueous liquid. Such compositions may be prepared by any suitable method of pharmacy which includes the step of bringing into association the extract of the present invention and one or more suitable carriers (which may contain one or more accessory ingredients as noted below). In general, the compositions of the invention are prepared by uniformly and intimately admixing the extract with a liquid or finely divided solid carrier, or both, and then, if necessary, shaping the resulting mixture. For example, a tablet may be prepared by compressing or moulding a powder or granules containing the extract, optionally with one or more accessory ingredients.

Compressed tablets may be prepared by compressing in a suitable machine, the extracts in the form of a powder or granules, optionally mixed with a binder, lubricant, inert diluents, and/or surface active/dispersing agent(s). Moulded tablets may be made by moulding, in a suitable machine, the powdered compound moistened with an inert liquid binder.

Suitable carriers may be fillers, such as sugars, for example lactose, saccharose, mannitol or sorbitol, cellulose preparations and/or calcium phosphates, for example, tricalcium phosphate or calcium hydrogen phosphate, and also binders, such as starch pastes using for example, corn, wheat, rice, or potato starch, gelatin, tragacanth, methylcellulose and/or polyvinylpyrrolidone and, if desired, disintegrators, such as the above-mentioned starches, also carboxymethyl starch, cross linked polyvinylpyrrolidone, agar or algin acid or a salt thereof, such as sodium alginate.

Excipients may be flow conditioners and lubricants, for example silicic acid, talc, stearic acid or salts thereof, such as magnesium or calcium stearate, and/or polyethylene glycol. Dragee cores are provided with suitable, optionally enteric coatings, there being used, inter alia, concentrated sugar solutions which may comprise gum Arabic, talc, polyvinylpyrrolidone, polyethylene glycol and/or titanium dioxide, or coating solutions in suitable organic solvents or solvent mixtures, or for the preparation of enteric coatings, solutions of suitable cellulose preparations, such as acetylcellulose phthalate or hydroxypropylmethylcellulose phthalate. Dyes or pigments may be added to the tablets or dragee coatings, for example, for identification purposes or to indicate different doses of active ingredients.

Formulations suitable for buccal (sublingual) administration include lozenges comprising the extracts in a flavoured base, usually sucrose and acacia or tragacanth; and pastilles comprising the extract in an inert base such as gelatine and glycerin or sucrose and acacia.

Compositions of the present invention suitable for parenteral administration conveniently comprise sterile aqueous preparations of the extracts, which preparations are preferably isotonic with the blood of the intended recipient. These preparations are preferably administered intravenously, although administration may also be effected by means of subcutaneous, intramuscular, or intradermal injection. Suitable compositions include water soluble extracts and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions comprising viscosity-increasing substances, for example sodium carboxymethylcellulose, sorbitol and/or dextran, and, where appropriate, also stabilizers. As an example, compositions may conveniently be prepared by admixing the extracts with water or a glycine buffer and rendering the resulting solution sterile and isotonic with the blood. Injectable formulations according to the invention may contain from 0.1% to 60% of the extract and may, for example, be administered at a rate of 0.1 ml/minute/kg.

Formulations suitable for rectal administration are preferably presented as unit dose suppositories. These may be prepared by admixing the extracts with one or more conventional solid carriers, for example cocoa butter, then reshaping the resulting mixture.

Compositions suitable for transdermal administration may be presented as discrete patches adapted to remain intact with the epidermis of the recipient for a prolonged period of time. Such patches may contain the extracts in an optionally buffered aqueous solution.

Compositions suitable for transdermal administration may also be delivered by iontophoresis (see, for example, Pharmaceutical Research 3 (6): 318 (1986) and typically take the form of an optionally buffered aqueous solution of the extracts, Such compositions may, for example, contain citrate or bis/tris buffer (pH6) or ethanol/water, with for example 0.05% to 30% w/w extract.

Compositions may be prepared in a manner, and in a form/amount as is conveniently practiced. See, for example, Goodman & Gillman, The Pharmacological Basis of Therapeutics (7$^{th}$ Edition, 1985) and Remington's Pharmaceutical Science (Mack Publishing Company, 10$^{th}$ Edition), both of which are incorporated herein by reference.

Compositions may contain, for example, from 0.1 mg to 2 g OPP such as 0.1 mg to 200 mg, more particularly 15 mg to 50 mg OPP.

The compositions of the invention may also be administered to a human in a dietary supplement form. Dietary supplements incorporating the active composition can be prepared by adding the composition to a food in the process of preparing the food. Any food may be used including, but not limited thereto, meats such as ground meats, emulsified meats and marinated meats; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen deserts, and non dairy frozen deserts; yoghurts; soaps; puddings; bakery products; salad dressings; and dips and spreads such as mayonnaise, butter, butter substitute, and other fat containing spreads. The composition is added to the food in an amount selected to deliver a desired dose of the composition to the consumer of the food.

An effective amount of the compositions of the present invention is administered to a human subject. The actual dosage levels will depend upon the a number of factors, such as specific mode of administration, the condition being treated, the condition of the patient and the judgement of the health care giver. Examples of dosages of the composition of the present invention are about 0.1 mg to about 200 mg per day, such as in the order of 1.5 mg/kg (body weight)/day. A convenient dosage form contains about 25 mg to 50 mg OPP as described herein.

The composition comprising OPP of the present invention may be prepared for use in a pharmaceutically effective or nutraceutically effective amount, solely on its own or in combination with other agents or compounds deemed appropriate by a person skilled in the art.

It is noted that the term 'pharmaceutically effective' and 'nutraceutically effective' amount includes a quantification that is acceptable for improving vascular health, treating and preventing vascular diseases and diseases related thereto.

In one embodiment the composition comprising OPP may be administered in form of doses, within a predetermined period of time, whereby it may be administered for example but not limiting to daily, weekly or monthly.

In another embodiment the composition comprising OPP may be provided in conventional treatment forms, pharmaceutical formulations or as nutritional supplement.

In one embodiment the composition of the present invention may be provided in a nutraceutical form.

The compositions according to the present invention may include one or more pharmaceutically acceptable or nutraceutically acceptable carriers. Carriers are selected so as to be acceptable in the sense of being ingredients in the composition and must not be deleterious to the patient. The carriers may be solid or a liquid, or both, and may be formulated with an extract containing the OPP at the desired ratios as a unit does, for example a tablet, which may contain from 0.5% to 80% by weight of the extract or up to 100% by weight of extract.

Compositions may be prepared by any of the well known techniques of pharmacy, for example admixing the extract, optionally including excipients, diluents (for example water) and auxiliaries as are well known in the pharmaceutical field. The compositions may include one or more agents, such as vitamins (for example, Vitamin A, Vitamin B group, Vitamin C, Vitamin D, Vitamin E and Vitamin K), and minerals (for example magnesium, iron, zinc, calcium and manganese in the form of pharmaceutically or nutraceutically acceptable salts).

It is noted from the results of the studies referred herein as exemplifications evidently show that the composition comprising OPP of the present invention have the following properties: promoting vascular health, improving vascular integrity thus limiting adherence of cells and build up of fatty plaques, inducing vasodilatation, reducing overall oxidative burden, limiting and thus inhibiting the oxidation of LDL cholesterol, inhibiting atheroma formation, lowering blood pressure, reducing cardiac and vascular hypertrophy, improving renal function, providing cardioprotective effect, preventing atherogenesis, and maintaining heart rhythm at normal rate in event that the blood flow is impaired or disrupted.

It is understood by a person skilled in the art that the methods for experiments and studies are described as exemplifications herein and thus the results are not intended, however, to limit or restrict the scope of the invention in any way and should not be construed as providing conditions, parameters, agents or starting materials which must be utilized exclusively in order to practice the present invention. It is therefore understood that the invention may be practiced, within the scope of the appended claims, with equivalent methods for the experiments than as specifically described and stated in claims.

The invention claimed is:

1. A composition for treating ventricular tachycardia (VT) comprising an effective amount of a freeze dried concentrate of an oil palm phenolics (OPP) extract,
wherein the OPP extract is a water soluble extract obtained from a vegetation liquor of a palm oil milling process,
wherein said freeze dried concentrate of the OPP extract has a strength of 30000 ppm GAE, and
wherein said composition is in a form selected from the group consisting of a capsule, a sachet, a lozenge, and a tablet.

2. A method for maintaining or promoting cardiovascular health of a subject, said method comprising regularly administering to said subject an effective amount of the composition according to claim 1.

3. The method of claim 2, wherein said subject is a healthy individual or animal.

4. A method for improving cardiovascular health of a subject, said method comprising regularly administering to said subject an effective amount of the composition according to claim 1.

5. The method of claim 4, wherein said subject is a healthy individual or animal.

6. A method for preventing the development of atherosclerotic lesions in a subject at risk therefor, said method comprising regularly administering to said subject an effective amount of the composition according to claim 1.

7. The method of claim 6, wherein said subject is a healthy individual or animal.

8. A method for protecting against cardiovascular disease, said method comprising regularly administering to a subject in need thereof an effective amount of the composition according to claim 1.

* * * * *